(12) United States Patent
Lanier et al.

(10) Patent No.: US 11,766,628 B2
(45) Date of Patent: Sep. 26, 2023

(54) PURIFICATION AND EXTRACTION OF CANNABINOIDS

(71) Applicant: CHEMTOR, LP, Lockhart, TX (US)

(72) Inventors: William Lanier, West Jordan, UT (US); Scott Davis, Smithville, TX (US)

(73) Assignee: Chemtor, LP, Lockhart, TX (US)

( * ) Notice: Subject to any disclaimer, the term of this patent is extended or adjusted under 35 U.S.C. 154(b) by 13 days.

(21) Appl. No.: 17/455,747

(22) Filed: Nov. 19, 2021

(65) Prior Publication Data

US 2022/0072448 A1 Mar. 10, 2022

Related U.S. Application Data

(63) Continuation of application No. 17/330,504, filed on May 26, 2021.

(60) Provisional application No. 63/031,775, filed on May 29, 2020.

(51) Int. Cl.
*A61K 36/185* (2006.01)
*B01D 11/02* (2006.01)
*C07C 39/04* (2006.01)

(52) U.S. Cl.
CPC ........ *B01D 11/0284* (2013.01); *A61K 36/185* (2013.01); *B01D 11/0288* (2013.01); *B01D 11/0292* (2013.01); *C07C 39/04* (2013.01)

(58) Field of Classification Search
CPC ............ B01D 11/0284; B01D 11/0288; B01D 11/0292; B01D 11/0488; B01D 11/0492; B01D 11/04; B01D 11/0415; B01D 2011/005; C07C 39/04; C07C 39/23;
(Continued)

(56) References Cited

U.S. PATENT DOCUMENTS

| | | |
|---|---|---|
| 7,618,544 B2 | 11/2009 | Massingill, Jr. |
| 8,128,825 B2 | 3/2012 | Massingill |
| 10,413,845 B1 * | 9/2019 | Tegen ................ B01D 11/0288 |

(Continued)

FOREIGN PATENT DOCUMENTS

CN 103865640 A 6/2014

OTHER PUBLICATIONS

International Search Report and Written Opinion of the International Search Authority issued by the U.S. Patent and Trademark Office for International Application No. PCT/US2021/034396 dated Oct. 12, 2021. (9 pages).

*Primary Examiner* — Joseph W Drodge
(74) *Attorney, Agent, or Firm* — HAYNES AND BOONE, LLP (57) ABSTRACT

A method for purification and extraction of cannabinoids includes: providing a cannabis oil including phospholipids and cannabinoid acids; contacting the cannabis oil with a degumming solvent, wherein the degumming solvent and cannabis oil are substantially immiscible; and separating an aqueous phase including the degumming solvent and at least a portion of the phospholipids from an oil phase including the cannabis oil. The method may further include contacting the oil phase with an extraction solvent, where the extraction solvent and oil phase are substantially immiscible; and separating an aqueous phase including the extraction solvent and at least a portion of the cannabinoid acids from a second oil solvent phase including the oil phase and/or simply the liberated cannabinoids following acidification of the extraction solvent.

18 Claims, 3 Drawing Sheets

(58) Field of Classification Search
CPC ..... C07C 2601/16; C07C 37/72; C07C 51/48; C07C 65/21; A61K 36/185
See application file for complete search history.

(56) References Cited

U.S. PATENT DOCUMENTS

| | | |
|---|---|---|
| 2012/0276265 A1 | 11/2012 | Crank |
| 2015/0017400 A1 | 1/2015 | Morgenstern et al. |
| 2017/0014733 A1 | 1/2017 | Massingill |
| 2018/0042845 A1* | 2/2018 | Sinai ................... A61K 31/352 |
| 2018/0134987 A1 | 5/2018 | Fedor et al. |
| 2020/0071285 A1 | 3/2020 | Tegen et al. |
| 2020/0199055 A1* | 6/2020 | Jansen ................. C07D 311/78 |
| 2020/0306219 A1* | 10/2020 | Kulpa ....................... A61K 9/08 |
| 2021/0053902 A1* | 2/2021 | Carraher ............... C07C 51/445 |
| 2022/0072448 A1* | 3/2022 | Lanier ..................... C07C 37/72 |

\* cited by examiner

PURIFICATION AND EXTRACTION OF CANNABINOIDS

CROSS-REFERENCE TO RELATED APPLICATIONS

This application is a Continuation of U.S. patent application Ser. No. 17/330,504, filed May 26, 2021, which claims priority to U.S. Provisional Application No. 63/031,775 filed May 29, 2020, the contents of which are herein incorporated in their entirety.

TECHNICAL FIELD

The present disclosure is related to purification and extraction of cannabinoids. More particularly, this disclosure is related to methods and systems of degumming cannabis oils and isolating cannabinoid acids from neutral cannabinoids.

BACKGROUND

Cannabinoids occur in the hemp plant, *Cannabis sativa*, primarily in the form of cannabinoid carboxylic acids (referred to herein as "cannabinoid acids"). "Neutral cannabinoids" are derived by decarboxylation of their corresponding cannabinoid acids. The more abundant forms of neutral cannabinoids include tetrahydrocannabinol (THC), cannabidiol (CBD), cannabichromene (CBC), and cannabigerol (CBG). Other neutral cannabinoids include, but are not limited to, cannabidivarin (CBDV), cannabichromevarin (CBCV), cannabigerovarin (CBGV), cannabielsoin (CBE), cannabicyclol (CBL), cannabivarin (CBV), cannabitriol (CBT), tetrahydrocannibivarin (THCV), cannabigerol monomethyl ether (CBGM), nabilone, and rimonabant.

Oil extracts from the *Cannabis sativa* plant ("cannabis oil") contain a mixture of cannabinoid acids and neutral cannabinoids along with other naturally occurring components, such as terpenes, terpenoids, sterols (such as phytosterols), triglycerides, alkanes, squalenes, tocopherols, carotenoids, flavonoids, polyphenols, cannflavins, and alkaloids. Although neutral cannabinoids are considered more physiologically active, many of the foregoing components have independent utility. For instance, tetrahydrocannabinolic acid (THCA) and cannabidiolic acid (CBDA) have been used in treating chronic conditions such as ALS, Fibromyalgia, Multiple Sclerosis as well as in patients suffering from neuropathy, pain, anxiety, inflammation, and/or seizures.

Currently, processing of cannabis typically includes a preliminary step of decarboxylating the cannabinoid acids to form neutral cannabinoids. This is due to the desirability of the neutral cannabinoids and the difficulty of separating the cannabinoid acids from the neutral cannabinoids in the absence of heat. As such, cannabinoid acid isolates are rarely available on the market and, if available, are very expensive.

Decarboxylation of cannabinoid acids is commonly achieved by heating the plant material or cannabis oil to convert cannabinoid acids to neutral cannabinoids and as such, the common practice of distillation fails to preserve the natural compounds endogenous to the plant. This method does not allow for isolation of cannabinoid acids and may result in denaturing or loss of other components, such as the terpenes, terpenoids, flavonoids, and other components discussed above. Accordingly, there remains a need for an economical method of separating cannabinoid acids from neutral cannabinoids.

DETAILED DESCRIPTION

The following descriptions are provided to explain and illustrate embodiments of the present disclosure. The described examples and embodiments should not be construed to limit the present disclosure.

It is commonly desirable to remove gums from plant oils. This can be achieved through a variety of techniques. Two of the most common methods of degumming involve the use of an aqueous acid (e.g., hydrochloric acid, citric acid, phosphoric acid, and the like) to convert the gums into water soluble molecules or steam distillation to remove fatty acids and gums. The gums include phospholipids such as phosphatides, which create problems during distillation (e.g., causing instability of the cannabis oil).

Figure 1:
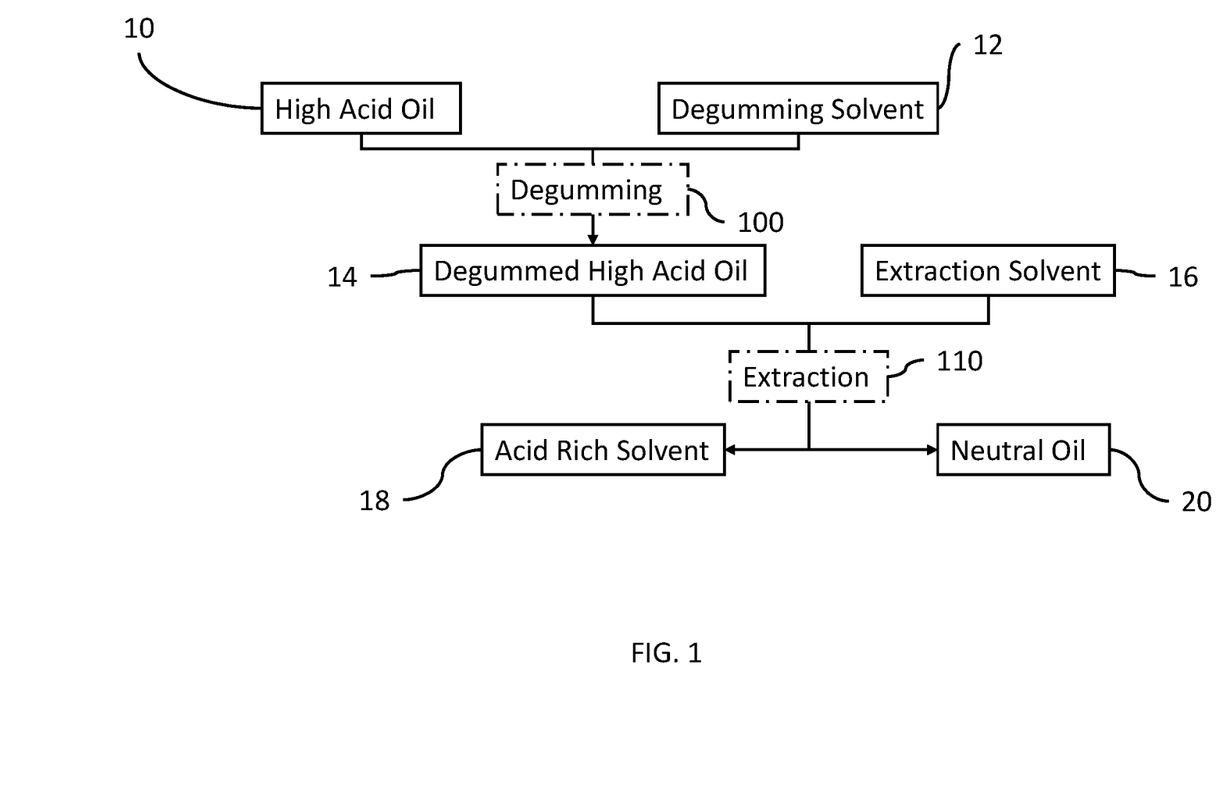
FIG. 1 is a diagram of an extraction and purification process according to an embodiment of the present disclosure.

With reference to FIG. 1, a process according to an embodiment of the present disclosure may include an initial step of contacting a high acid oil 10 with a degumming solvent 12 through degumming 100. Degumming 100 serves a dual purpose of both removing unwanted gums from the high acid oil 10 and enriching the cannabinoid concentration within the high acid oil 10.

The high acid oil 10 comprises an oil extracted from the *Cannabis sativa* plant and may have a content of cannabinoids of, for example, 1-99% (w/w), 10-90%, 20-85%, 30-80%, 50-80%, 60-80%, or 65-75%. In one or more embodiments, a weight ratio of cannabinoid acids to neutral cannabinoids in the high acid oil 10 is at least 1, at least 2, at least 2.5 at least 3, at least 3.5, at least 4, at least 10, at least 25, at least 40, 0.5-50, 1-45, 1-40, 1-20, 1-10, 2-8, or 3-5. In one or more embodiments, the cannabinoid acids comprise CBDA, THCA, cannabigerolic acid (CBGA), cannabidivarinic acid (CBDVA), and/or cannabichromenic acid (CBCA). Any ratios described herein between cannabinoid acids and neutral cannabinoids may be based on a total weight of all cannabinoid acids and a total weight of all neutral cannabinoids or may be based on a weight of a single cannabinoid acid and a weight of the corresponding neutral cannabinoid (e.g., a weight ratio of CBDA:CBD, THCA:THC, CBGA:CBG, etc.).

According to one or more embodiments, the high acid oil 10 is diluted in a solvent prior to contacting the degumming solvent 12. According to some embodiments, the high acid oil 10 is diluted by a factor 2, 3, 4, or 5 in the solvent. The solvent comprises a polar and/or nonpolar solvent. In some embodiments, the solvent is a polar solvent and comprises ethyl acetate, ethanol, acetone, water, benzyl alcohol, 1,3-butylene glycol, citric acid esters of mono- and di-glycerides, glycerol, glyceryl diacetate, glyceryl triacetate, glyceryl tributyrate, isopropanol, methanol (no more than 50 ppm), 2-butanone (no more than 50 ppm), 1,2-propanediol, propylene glycol mono-esters and diesters of fatty acids, mono- and di-glycerides, triethyl citrate, terpenes or combinations thereof. In some embodiments, the solvent is a nonpolar solvent and typically comprises, but is not limited to: propane, butane, pentane, hexane, heptane, or combinations of these and other hydrocarbons of varying length; being either branched or unbranched. When the high acid oil 10 is an ethanol extracted oil, the solvent may include ethanol. This ensures that all the material in the ethanol extracted high acid oil 10 is dissolved, thereby preventing yield loss. High acid oil 10 extracted with nonpolar solvents (e.g., propane, butane, pentane, and/or heptane) may not require dilution with ethanol. In one or more embodiments, the high acid oil 10 is an ethanol extracted oil and is diluted by a factor of 4 with 70 wt % heptane and 5 wt % ethanol (25 wt % high acid oil 10) prior to contacting with the degumming solvent 12. In one or more embodiments, the diluted high acid oil 10 comprises at most 15 wt %, at most 10 wt %, at most 7 wt %, or at most 5 wt % of ethanol. In some embodiments, the diluted high acid oil 10 may be winterized (i.e., chilled to 20° C. or below for 8-12 hours) and filtered to remove undesirable components (such as waxes and/or carbohydrates).

The degumming solvent 12 is substantially immiscible with the high acid oil 10. In one or more embodiments, the degumming solvent 12 comprises an aqueous acid, such as hydrochloric acid, citric acid, and/or phosphoric acid. A concentration of the acid may be, for example, 1-30 wt %, 5-20 wt %, 5-15 wt % or 8-12 wt %. In one or more embodiments, the degumming solvent 12 is 10 wt % aqueous citric acid.

Contacting the degumming solvent 12 and the high acid oil 10 during degumming 100 involves two-phase chemistry, wherein the high acid oil 10 and the degumming solvent 12 are substantially immiscible. A chemical reaction and/or mass transfer occurs at interfaces between the two phases. The contacting may be achieved using any two-phase chemistry device or fractioning process including but not limited to a stirred pot, a conduit contactor, and/or chromatography (such as HPLC, NPLC, CRC, or RPLC). Examples of conduit contactors (also sometimes referred to as fiber conduit contactors or fiber reactors) are described in U.S. Pat. Nos. 7,618,544 and 8,128,825, both of which are incorporated by reference herein in their entireties. In one or more embodiments, the contacting for two-phase chemical reactions is performed in a fiber conduit contactor. The present disclosure demonstrates the desirability of using a fiber conduit contactor in the two-phase chemical reactions described herein due to, for example, the high levels of cannabinoid enrichment achievable and the efficient isolation of cannabinoid acids from neutral cannabinoids.

During degumming 100, the gums are removed from the high acid oil 10 into the degumming solvent 12, thereby producing a degummed high acid oil 14. Namely, degumming 100 produces an oil phase (degummed high acid 14) and an aqueous phase (degumming solvent 12 with gums dissolved therein) that may be separated from one another by known methods. It should be noted that although this step 100 further enriches the product, degumming in and of itself is not a mandatory step that must precede extraction 110. Likewise, the degumming process 100 can be performed post extraction 110 or omitted altogether. However, in the preferred embodiment, it is included as part of the process.

In some embodiments, by only removing non-cannabinoid components (i.e., gums) from the high acid oil 10, degumming 100 enriches the cannabinoids. In one or more embodiments, degumming 100 results in cannabinoid enrichment (calculated as [cannabinoid content (in wt %) in degummed high acid oil 14—original cannabinoid content in high acid oil 10]/original cannabinoid content) of at least 0.5%, at least 1%, at least 2%, at least 3%, at least 4%, at least 5%, 0.5-5%, 1-5%, or 2-4.5%.

In one or more embodiments, degumming 100 is omitted or is conducted by an alternative method, such as steam distillation.

According to the embodiment shown in FIG. 1, the degummed high acid oil 14 undergoes an extraction 110, wherein the degummed high acid oil 14 is contacted with an extraction solvent 16. Extraction 110 involves two-phase chemistry and may use any of the devices/processes mentioned above with respect to degumming 100.

The extraction solvent 16 is substantially immiscible with the degummed high acid oil 14. In one or more embodiments, the extraction solvent 16 comprises water, alcohol, and a base. The alcohol is not particularly limited and may include ethanol, methanol, isopropanol, and/or butanol. In some embodiments, the alcohol is ethanol since ethanol is safe for human consumption. The base is not particularly limited and may include, for example, sodium hydroxide, potassium hydroxide, calcium hydroxide, ammonium hydroxide, sodium carbonate, sodium bicarbonate, potassium carbonate, potassium bicarbonate and or a combination of bases. In one or more embodiments, the extraction solvent 16 comprises 50-99 wt %, 60-95 wt %, 65-90 wt %, 70-85 wt %, 70-80 wt %, or 60-75 wt % of water. In some embodiments, the extraction solvent 16 comprises 5-40 wt %, 5-30 wt %, 10-30 wt %, 15-25 wt %, 15-30 wt %, 25-30 wt %, or 20-30 wt % of the alcohol. In some embodiments, the extraction solvent 16 comprises 0.1-10 wt %, 0.25-5 wt %, 0.5-5 wt %, 1-3 wt %, or 1.5-2.5 wt % of the base.

Through extraction 110, cannabinoid acids in the degummed high acid oil 14 are removed into the extraction solvent 16, thereby producing an acid rich solvent 18 and a neutral oil 20. In one or more embodiments, the neutral oil 20 has a weight ratio of cannabinoid acids to neutral cannabinoids of less than 50, less than 40, less than 25, less than 10, less than 5, less than 4, less than 3, less than 2, less than 1, less than 0.5, or 0 (i.e., substantially no cannabinoid acids). In one or more embodiments, the weight ratio of cannabinoid acids to neutral cannabinoids in the neutral oil 20 is no more than 0.8 times, no more than 0.7 times, no more than 0.5 times, no more than 0.33 times, or no more than 0.2 times the weight ratio of cannabinoid acids to neutral cannabinoids in the high acid oil 10.

Figure 2:
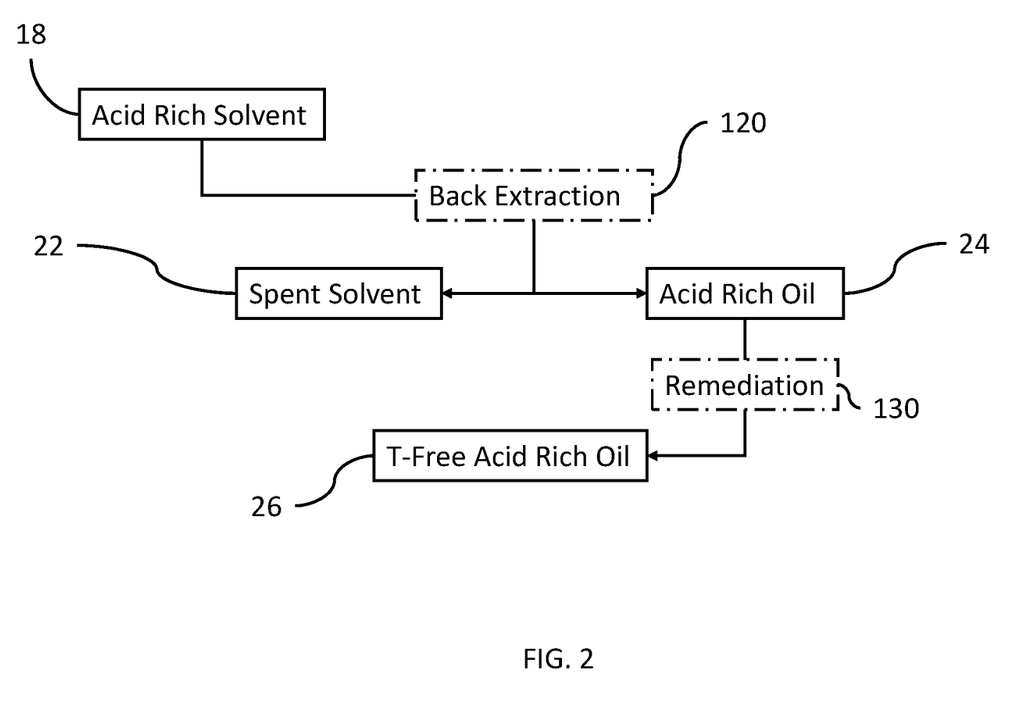
FIG. 2 is a diagram of an extraction and purification process according to an embodiment of the present disclosure.

With reference to FIG. 2, the acid rich solvent 18 may undergo back extraction 120, wherein the acid rich solvent 18 is mixed with an oil and/or solvent and the cannabinoid acids are back extracted following acidification of the acid rich solvent using an appropriate aqueous acid such as hydrochloric, phosphoric, sulfuric or acetic acid. The oil and/or solvent used to back extract is not particularly limited. In some embodiments, the oil and/or solvent comprises medium-chain triglycerides (MCT), olive oil, soybean oil, canola oil, cotton oil, palmolein, sunflower oil, corn oil, rapeseed oil, grape seeds oil, hemp oil, pomegranate oil, avocado oil, peppermint oil, tomato oil, isopropyl myristate, oleyl lactate, coco caprylocaprate, hexyl laurate, oleyl amine, oleic acid, oleyl alcohol, linoleic acid, linoleyl alcohol, ethyl oleate, D-limonene, neem oil, lavender oil, peppermint oil, anise oil, rosemary oil, sage oil, hibiscus oil, berries oil (any type), menthol, capsaicin, grape seed oil, pumpkin oil, hemp oil and similar essential oils or triglycerides or esters of fatty acids, heptane, hexane, pentane, suitable water immersible hydrocarbons, and/or mixtures thereof.

Back extraction 120 involves two-phase chemistry and may use any of the devices/processes mentioned above with respect to degumming 100 and extraction 110. Back extraction 120 results in an oil phase (acid rich oil 24 including cannabinoid acids) and an aqueous phase (spent solvent 22) that may be separated by known methods. The acid rich oil 24 may undergo further processing, such as remediation 130 (i.e., removal of THCA) to form T-free acid rich oil 26 or further processes using chromatography to separate out distinct cannabinoids. In some embodiments, the T-free acid rich oil 26 is free of, or substantially free (less than 0.3% by weight) of psychoactive cannabinoids. In another embodiment, the T-free acid rich oil 26 contains psychoactive cannabinoids in an amount that does not provide a discernable psychoactive effect when administered to a subject. In some embodiments, the individual cannabinoid acids may be isolated from acid rich oil 24 or the T-free acid rich oil 26 via, for example, chromatography.

In one or more embodiments, the rich oil 24 has a weight ratio of cannabinoid acids to neutral cannabinoids of at least 5, at least 6, at least 10, at least 20, at least 25, at least 40, or at least 50. In one or more embodiments, the weight ratio of cannabinoid acids to neutral cannabinoids in the acid rich oil 24 is at least 2 times, at least 5 times, at least 10 times, or at least 15 times the weight ratio of cannabinoid acids to neutral cannabinoids in the high acid oil 10.

Figure 3:
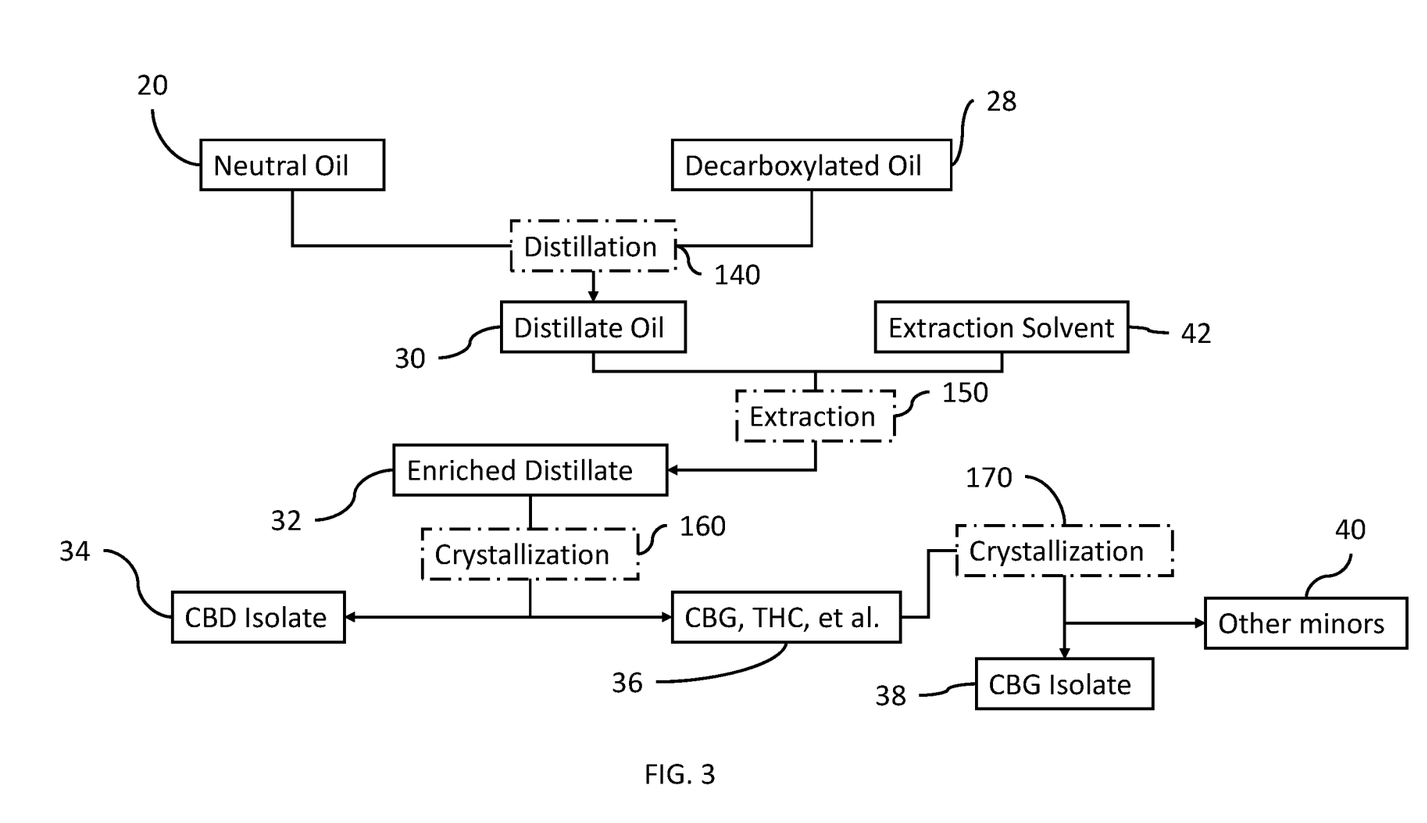
FIG. 3 is a diagram of an extraction and purification process according to an embodiment of the present disclosure.

Referring to FIG. 3, the neutral oil 20 may undergo further processing to extract or separate the constituent components thereof, such as THC, CBD, CBG or any other major or minor cannabinoids present in this collection. In the embodiment shown in FIG. 3, the neutral oil 20 undergoes distillation 140 to form a distillate oil 30. As shown, decarboxylated oil 28 from other sources (e.g., heat treated high acid oil) may likewise undergo distillation 140. In some embodiments, the neutral oil 20 may be combined with decarboxylated oil 28 prior to further processing. The distillate oil 30 may be contacted with an extraction solvent 42 in extraction 150 to form an enriched distillate 32. The extraction solvent 42 may be, for example, the same as the extraction solvent 16 described herein. The extraction 150 may utilize two-phase chemistry, as discussed in detail above. The enriched distillate 32 may undergo crystallization 160 whereby a CBD isolate 34 is removed, leaving a remainder 36, which may undergo chromatography and/or further crystallization 170 to remove CBG 38 and or isolates of other cannabinoids 40 present. Other minor components 40 may be of value as is, or may be further processed, enriched, or isolated.

EXAMPLES

Example 1

Miscella were prepared from commercially available ethanol extracted cannabis oils by mixing with heptane and ethanol with a final target solution composition of 70 wt % heptane, 5 wt % ethanol, and 25 wt % cannabis oil. The miscella were decanted and then filtered through diatomaceous earth and a one-micron filter paper. The filtrate was then chilled to −20° C. overnight and decanted again. The miscella were run through a fiber conduit contactor with 10% citric acid in distilled water. The experimental conditions and results are summarized in Table 1 below.

TABLE 1

Degumming of crude cannabis oil miscella using a fiber conduit contactor

| Type of Oil | Ex. 1A: Cryo-Ethanol High Acid (B7) | Ex. 1B: Cryo-Ethanol Decarb (B3) | Ex. 1C: Cryo-Ethanol High Acid (B7) |
|---|---|---|---|
| Miscella Solvent | Heptane/Ethanol (70/5) | Heptane/Ethanol (70/5) | Ethyl acetate |
| Flow Rates | 40 mL/min Miscella 80 mL/min Citric acid | 40 mL/min Miscella 80 mL/min Citric acid | 80 mL/min Miscella 80 mL/min Citric acid |
| Starting Cannabinoid Concentration (wt %) | 71.4% | 73.9% | 71.4% |
| Final Cannabinoid concentration (wt %) | 74.5% | 75.0% | 71.2% |
| Enrichment | 4.3% | 1.5% | −0.3% |

As shown in Table 1, using ethyl acetate as a solvent for miscella interfered with the degumming process. Also, although the Example 1B (using decarboxylated cannabis oil) had a higher starting cannabinoid concentration, the degumming process enriched the high acid sample (Example 1A) by 4.3% as compared to 1.5% for Example 1B.

Example 2

Degummed miscella from Example 1A were used to investigate the extraction of acid cannabinoids into a water/ethanol solvent using a fiber conduit contactor. Bases tested included sodium bicarbonate ($NaHCO_3$), sodium carbonate ($Na_2CO_3$), potassium bicarbonate ($KHCO_3$), and potassium carbonate ($K_2CO_3$). These were selected for their varied pH, ionic strength, ionic radii, and solubility properties, listed in Table 2 below. The hardness difference between a sodium and potassium radii (smaller radii are harder, larger radii are softer) creates a variation in the property of the resulting soaps. Sodium salts give a so-called "harder" soap that is more likely to be rejected from the crude miscella. Switching from bicarbonate to carbonate has two effects: (1) higher ion count in solution, thereby increasing ionic strength/polarity; and (2) increasing the pH by approximately 1 pH unit for the same wt % solution. This increased polarity can be used to enforce selectivity of the desired compounds.

TABLE 2

| Salt | $NaHCO_3$ | $Na_2CO_3$ | $KHCO_3$ | $K_2CO_3$ |
|---|---|---|---|---|
| pKa of Conjugate acid | 3.6 | 10.3 | 3.6 | 10.3 |
| Ion Count per Mol | 2 | 3 | 2 | 3 |
| Cationic radii | 227 pm | 227 pm | 280 pm | 280 pm |

As shown in the results below, there are multiple options for extracting specific combinations of cannabinoids. The bicarbonate bases gave a preference to acid cannabinoids, whereas the stronger carbonate bases were able to increase the total mass transfer. These parameters can be used to control the outflow product streams. The partition coefficients for various combinations are summarized in Table 3 and can be used to determine the optimal extraction solvent for a target compound or goal.

It can be seen in the $Na_2CO_3$ experiments, a large amount of CBDA was moved out of the crude miscella into the extraction solvent. This, however, was at the expense of a lower overall extraction of cannabinoids. The best enrichment of total cannabinoids can be seen by comparing the largest difference between the non-cannabinoid material and the cannabinoid material columns. In the Examples summarized in Table 3 below, the largest difference in distribution is with a 70/30 water ethanol solution with a $NaHCO_3$ base (2%) wherein the extraction is almost exclusively CBDA, but this comes at the cost of very low extraction of cannabinoid materials overall. The selection of $K_2CO_3$ as a base in a 70/25 water/ethanol solvent is an excellent way to selectively remove acid cannabinoids from decarboxylated (neutral) forms.

TABLE 4

Results of various extraction solvents in partitioning CBDA from CBD.

| Target Objective | Acid partitioning | Enrichment | Enrichment |
|---|---|---|---|
| Extraction Solvent | 75/25:2.0 Water/Ethanol: Potassium Carbonate | 75/25:2.5 Water/Ethanol: Sodium Bicarbonate | 80/20:2.0 Water/Ethanol: Sodium Bicarbonate |
| Crude Oil Cannabinoid Concentration (w/w %) | 71.2 | 77.1 | 66.9 |
| Ratio of CBDA to CBD in Crude Oil | 3.6 | 3.6 | 3.4 |
| Neutral Oil Cannabinoid Concentration (w/w %) | 68.2 | 82.0 | 71.9 |
| Ratio of CBDA to CBD in Neutral Oil | 0.0 | 1.6 | 2.5 |

TABLE 3

Partition coefficients for selected cannabinoids.

| Base | $H_2O$/EtOH/Base (wt %) | Non-Cannabinoid | Total Cannabinoid | CBDA | CBGA | THCA | CBCA | CBG | CBD | THC | CBC |
|---|---|---|---|---|---|---|---|---|---|---|---|
| $NaHCO_3$ | 67.8/29.7/2.4 | | 0.46 | 0.43 | 0.46 | 0.91 | 0.57 | 0.46 | 0.48 | 0.77 | 0.54 |
| $NaHCO_3$ | 72.9/24.6/2.5 | 0.55 | 0.73 | 0.68 | 0.76 | 1 | 1.14 | 0.76 | 0.78 | 1.03 | 0.83 |
| $NaHCO_3$ | 77.9/19.6/2.5 | 0.42 | 1.17 | 1.09 | 1.2 | 1.33 | | | 1.29 | 1.43 | 1.42 |
| $NaHCO_3$ | 81.2/16.3/2.5 | 0.33 | 1.11 | 1.05 | 1.19 | 1.16 | 1.24 | | 1.25 | 1.28 | 1.33 |
| $NaHCO_3$ | 879./9.7/2.4 | 0.42 | 1.02 | 0.96 | 1.1 | 1.12 | 1.17 | | 1.14 | 1.17 | 1.21 |
| $K_2CO_3$ | 68.3/29.1/2.5 | −0.53 | 0.21 | 0.04 | 0.15 | 0.28 | 0.22 | | 0.55 | 0.59 | 0.6 |
| $K_2CO_3$ | 73.0/24.5/2.5 | −0.56 | 0.62 | 0.45 | | | | | 0.87 | | |
| $K_2CO_3$ | 77.9/19.5/2.6 | −0.22 | −0.06 | −0.16 | −0.19 | −0.09 | −0.29 | 0.01 | 0.19 | 0.19 | 0.23 |
| $K_2CO_3$ | 82.8/14.7/2.5 | −0.2 | −0.01 | −0.08 | −0.15 | −0.05 | −0.25 | 0.05 | 0.19 | 0.09 | 0.23 |
| $K_2CO_3$ | 87.5/10/2.5 | −0.13 | 0.03 | 0 | −0.1 | 0.15 | −0.2 | −0.07 | 0.1 | 0.13 | 0.16 |
| $Na_2CO_3$ | 68.4/29.1/2.5 | 0.12 | −0.78 | −2.37 | −0.57 | −0.18 | 0.93 | 1.58 | −0.87 | 0.22 | −0.2 |
| $Na_2CO_3$ | 73.2/24.2/2.6 | 0.28 | −0.59 | −2.22 | −0.47 | −0.02 | 1.09 | 1.6 | −0.86 | 0.2 | −0.16 |
| $Na_2CO_3$ | 77.6/19.9/2.5 | 0.26 | −0.57 | −2.22 | −0.5 | −0.02 | 1.08 | 1.53 | −0.94 | 0.1 | −0.21 |
| $Na_2CO_3$ | 82.9/14.5/2.6 | 0.31 | −0.47 | −2.11 | −0.44 | 0.06 | 1.15 | 1.59 | −0.9 | 0.13 | −0.14 |
| $Na_2CO_3$ | 87.8/9.7/2.6 | 0.46 | −0.09 | −1.75 | −0.14 | 0.41 | 1.48 | 1.91 | −0.55 | 0.47 | 0.22 |
| $KHCO_3$ | 68.1/29.4/2.6 | 1.43 | 0.57 | −1.02 | 0.33 | 1.26 | 2.09 | | 0.6 | | |
| $KHCO_3$ | 73.1/24.3/2.6 | 0.99 | 1.02 | −0.59 | 0.72 | 1.76 | 2.59 | | 1.06 | | |
| $KHCO_3$ | 78.0/19.5/2.5 | 1.87 | 1.65 | 0.04 | 1.4 | | | | 1.59 | | |
| $KHCO_3$ | 82.7/14.8/2.5 | 1.11 | 1.8 | 0.21 | 1.61 | | | | 1.43 | | |
| $KHCO_3$ | 86.3/11.3/2.5 | | 1.26 | 0.19 | | | | | | | |
| $NaHCO_3$ | 68.4/29.5/2.0 | 3.12 | 1.4 | −0.19 | | | | | 1.4 | | |
| $NaHCO_3$ | 69.0/29.6/1.5 | 2.18 | 1.71 | 0.1 | | | | | 1.86 | | |
| $NaHCO_3$ | 69.2/29.8/1.0 | 1.81 | 1.85 | 0.22 | | | | | | | |
| $NaHCO_3$ | 69.6/29.8/0.5 | 1.9 | 1.96 | | | | | | | | |
| $NaHCO_3$ | 69.9/29.9/0.25 | 2.27 | 2.02 | 0.38 | | | | | 2.62 | | |

In Table 3 above, the Examples are ordered by decreasing polarity from top to bottom. A lower number specifies a preference for extraction and a high number specifies a preference to remain in the neutral oil. Blank squares are where coefficients could not be calculated.

These tests show a highly effective separation of the acid forms, leaving no CBDA behind in the neutral oil (see Table 4 below). If selectivity of acid forms is less of a priority and increased purity is the target, 2.0% $NaHCO_3$ in 80/20 waterethanol provides a reduced extraction rate, but the highest enrichment, moving the ratio of CBDA to CBD from 3.6:1 in the crude oil to 52.9:1 in the enriched oil, as shown in Table 4. In Table 4 below, the crude oil is the starting material, rich oil is the extracted oil, and neutral oil is the starting material post-extraction.

TABLE 4-continued

Results of various extraction solvents in partitioning CBDA from CBD.

| Target Objective | Acid partitioning | Enrichment | Enrichment |
|---|---|---|---|
| Rich Oil Cannabinoid Concentration (w/w %) | 74.5 | 81.9 | 86.8 |
| Ratio of CBDA to CBD in Rich Oil | 31.7 | 52.9 | 18.3 |

Example 3

Solution based chemistry has been demonstrated anecdotally to effectively remove some non-cannabinoid materials from distillates. Due to the similar boiling points of some organic acids and cannabinoids, these acids seem like a likely impurity. Two-phase chemistry, either with or without fiber conduit contactors, has been established as an effective tool for the removal of organic acids from oil streams, e.g. removing free fatty acids from distiller's corn oil. To test the viability of the same chemistries for washing distillate, trial extractions were performed, as summarized in Table 5 below. These tests showed significant increases in cannabinoid concentration and suggest the value of solution-based chemistry.

TABLE 5

Solution washing of distillate for enrichment.

| 3:1 Ethyl Acetate: Distillate | Distillate Fraction 5 Total Cannabinoid Content/CBD Content | Distillate Fraction 6 Total Cannabinoid Content/CBD Content |
|---|---|---|
| Pre-Extraction Distillate Miscella | 48.7%/48.5% | 84.4%/73.6% |
| Post-Extraction Washed Miscella | 79.1%/73.9% | 94.5%/85.1% |

The enrichment of distillate was quite successful and resulted in a concentration of cannabidiol high enough for spontaneous crystallization and provides a cannabinoid rich material for THC remediation by chromatography. By removing the bulk of the non-cannabinoid material prior to remediation, throughput should be significantly increased.

The results of these studies suggest that specific two-phase chemistries can be combined with fiber conduit contactor technology to enhance cannabinoid purity, yield, or throughput. The process technology can be used to produce materials which are of interest on the market, and the partitioning of acid and neutral cannabinoids produces two separate product streams.

Benefits of the fiber conduit contactor/solution processing chemistry described herein include: the reduction of impurities that often foul distillation equipment (e.g., gums, waxes, carbohydrates, etc.), the enrichment of cannabinoid materials prior to chromatography or isolate preparations, and the production of commercial material with reduced degradation of terpenes, terpenoids, flavonoids, and other parts of the full spectrum of cannabis plant materials.

Although the present disclosure has been described using preferred embodiments and optional features, modification and variation of the embodiments herein disclosed can be foreseen by those skilled in the art, and such modifications and variations are considered to be within the scope of the present disclosure. It is also to be understood that the above description is intended to be illustrative and not restrictive. Many alternative embodiments will be apparent to those of in the art upon reviewing the above description. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the disclosure.

What is claimed is:

1. A method, comprising:
   providing a cannabis oil comprising neutral cannabinoids, cannabinoid acids, and phospholipids;
   contacting the cannabis oil with a degumming solvent, wherein the degumming solvent and cannabis oil are substantially immiscible;
   separating an aqueous phase comprising the degumming solvent and at least a portion of the phospholipids from a first oil phase comprising the cannabis oil less the at least a portion of the phospholipids;
   contacting the first oil phase with an extraction solvent, wherein the extraction solvent is basic, and the extraction solvent and the fir oil phase are substantially immiscible; and
   separating a second aqueous phase comprising the extraction solvent and at least a portion of the cannabinoid acids from a second oil phase comprising the first oil phase less the at least a portion of the cannabinoid acids.

2. The method according to claim 1, wherein the degumming solvent comprises 10 wt % citric acid in water.

3. The method according to claim 2, wherein contacting the cannabis oil with the degumming solvent comprises introducing the cannabis oil and the degumming solvent into a fiber conduit contactor.

4. The method according to claim 1, wherein, prior to contacting the cannabis oil with the degumming solvent, the cannabis oil is diluted in a solvent comprising a hydrocarbon and ethanol.

5. The method according to claim 4, wherein the cannabis oil is diluted with the solvent by a factor of at least 2.

6. The method according to claim 1, wherein a concentration by weight of the neutral cannabinoids in the first oil phase is at least 3% greater than a concentration by weight of the neutral cannabinoids in the cannabis oil.

7. The method according to claim 1, wherein the cannabinoid acids comprise cannabidiolic acid.

8. The method according to claim 1, wherein the extraction solvent comprises water, an alcohol, and a base.

9. The method according to claim 8, wherein the alcohol is ethanol and constitutes 5 to 30 wt % of the extraction solvent.

10. The method according to claim 8, wherein the base is selected from the group consisting of sodium hydroxide, potassium hydroxide, calcium hydroxide, ammonium hydroxide, sodium carbonate, sodium bicarbonate, potassium carbonate, potassium bicarbonate, and combinations thereof.

11. The method according to claim 1, wherein contacting the first oil phase with the extraction solvent comprises introducing the oil phase and the extraction solvent into a fiber conduit contactor.

12. The method according to claim 11, wherein separating the second aqueous phase from the second oil phase comprises separately removing the second aqueous phase and the second oil phase from a downstream end of the fiber conduit contactor.

13. The method according to claim 1, wherein a weight ratio of cannabinoid acids to neutral cannabinoids in the second oil phase is no more than 0.8 times a weight ratio of cannabinoid acids to neutral cannabinoids in the cannabis oil.

14. The method according to claim 1, wherein the cannabinoid acids comprise tetrahydrocannabinolic acid.

15. The method according to claim 1, wherein the cannabinoid acids comprise cannabigerolic acid.

16. The method according to claim 1, wherein the extraction solvent comprises 70-95 wt % water, 5-30 wt % ethanol, and 0.25-5 wt % of a base selected from sodium hydroxide, potassium hydroxide, calcium hydroxide, ammonium hydroxide, sodium carbonate, sodium bicarbonate, potassium carbonate, potassium bicarbonate, and combinations thereof.

17. A method, comprising:
providing a cannabis oil comprising neutral cannabinoids, cannabinoid acids, and phospholipids;
contacting the cannabis oil with a degumming solvent, wherein the degumming solvent and cannabis oil are substantially immiscible;
separating an aqueous chase comprising the degumming solvent and at least a portion of the phospholipids from a first oil phase comprising the cannabis oil less the at least a portion of the phospholipids;
contacting the oil phase with an extraction solvent, wherein the extraction solvent and the oil phase are substantially immiscible;
separating a second aqueous phase comprising the extraction solvent and at least a portion of the cannabinoid acids from a second oil phase comprising the first oil phase less the at least a portion of the cannabinoid acids;
acidifying the extraction solvent in the second aqueous phase with an aqueous acid, mixing the second aqueous phase with an oil or a solvent; and
A reprocessing the mixture to back extract the at least a portion of the cannabinoid acids from the aqueous extraction solvent.

18. The method according to claim 17, wherein a weight ratio of cannabinoid acids to neutral cannabinoids in the second oil phase is at least 2 times a weight ratio of cannabinoid acids to neutral cannabinoids in the cannabis oil.

* * * * *

UNITED STATES PATENT AND TRADEMARK OFFICE
CERTIFICATE OF CORRECTION

| | |
|---|---|
| PATENT NO. | : 11,766,628 B2 |
| APPLICATION NO. | : 17/455747 |
| DATED | : September 26, 2023 |
| INVENTOR(S) | : William Lanier and Scott Davis |

It is certified that error appears in the above-identified patent and that said Letters Patent is hereby corrected as shown below:

In the Specification

Column 7, Line 62, change "waterethanol" to --water ethanol--.

In the Claims

Column 10, Line 13, change "fir" to --first--.
Column 11, Line 12, change "chase" to --phase--.
Column 12, Line 9, delete "A".

Signed and Sealed this
Fourteenth Day of November, 2023

*Katherine Kelly Vidal*

Katherine Kelly Vidal
*Director of the United States Patent and Trademark Office*